United States Patent [19]
Ways

[11] Patent Number: 6,103,712
[45] Date of Patent: Aug. 15, 2000

[54] THERAPEUTIC TREATMENT FOR ASTHMA

[75] Inventor: Douglas Kirk Ways, Indianapolis, Ind.

[73] Assignee: Eli Lilly and Company, Indianapolis, Ind.

[21] Appl. No.: 09/253,716

[22] Filed: Feb. 22, 1999

Related U.S. Application Data

[60] Provisional application No. 60/076,850, Mar. 5, 1998.
[51] Int. Cl.$^7$ ..................................................... A61K 31/33
[52] U.S. Cl. ............................................ 514/183; 514/826
[58] Field of Search ...................... 514/183, 826

[56] References Cited

U.S. PATENT DOCUMENTS

| | | | |
|---|---|---|---|
| 5,057,614 | 10/1991 | Davis et al. | 548/466 |
| 5,481,003 | 1/1996 | Gillig et al. | 548/455 |
| 5,491,242 | 2/1996 | Gillig et al. | 548/455 |
| 5,545,636 | 8/1996 | Heath, Jr. et al. | 514/214 |
| 5,552,396 | 9/1996 | Heath, Jr. et al. | 514/183 |
| 5,559,228 | 9/1996 | Gillig et al. | 540/460 |
| 5,621,098 | 4/1997 | Heath, Jr. et al. | 540/472 |
| 5,710,145 | 1/1998 | Engel et al. | 514/183 |
| 5,780,461 | 7/1998 | Heath, Jr. et al. | 514/183 |

FOREIGN PATENT DOCUMENTS

| | | |
|---|---|---|
| 0 428 106 | 5/1991 | European Pat. Off. . |
| 0 588 762 | 3/1994 | European Pat. Off. . |
| 0 657 411 A1 | 6/1995 | European Pat. Off. . |
| 0 657 458 A1 | 6/1995 | European Pat. Off. . |
| 93 16703 | 9/1993 | WIPO . |
| 97 40830 | 11/1997 | WIPO . |
| 97 45397 | 12/1997 | WIPO . |

OTHER PUBLICATIONS

Wilkinson et al. "Isoenzyme specificity of bisindolylmaleimides, selective inhibitors of protein kinase C" Biochem J. (1993) 294 pp. 335–337.

*Primary Examiner*—Kimberly Jordan
*Attorney, Agent, or Firm*—Paul R. Darkes

[57] ABSTRACT

A method for treating asthma and disease conditions associated therewith is disclosed, particularly using the isozyme selective PKC inhibitor, (S)-3,4-[N,N'-1,1'-((2"-ethoxy)-3'''-(O)-4'''-(N,N-dimethylamino)-butane)-bis-(3,3'-indoly1)]-1(H)-pyrrole-2,5-dione and its pharmaceutically acceptable salts.

12 Claims, No Drawings

THERAPEUTIC TREATMENT FOR ASTHMA

This application claims the benefit of co-pending provisional application Ser. No. 60/076,850, filed Mar. 5, 1998, which is incorporated by reference herein.

BACKGROUND OF THE INVENTION

1. Field of the Invention

The present invention is broadly directed to a method for inhibiting pulmonary vascular permeability, bronchial smooth muscle contractility, and airway hyperactivity. The present invention is particularly directed to the use of a particular class of isozyme selective Protein Kinase C (PKC) inhibitors for treating asthma and the syndromes associated therewith.

2. Description of Related Art

Asthma is a disease of airways that is characterized by increased responsiveness of the tracheobronchial tree to a multiplicity of stimuli. Three percent of the population of the United States suffers from the disease. Similar figures have been reported from other countries. Bronchial asthma occurs at all ages but predominantly in early life. About one-half of the cases develop before age 10 and another third occur before age 40. In childhood, there is a 2:1 male/female preponderance which equalizes by age 30. The common denominator underlying the asthmatic diathesis is a nonspecific hyperirritability of the tracheobronchial tree.

We believe protein kinase C (PKC) is involved in the signal transduction pathways that mediate the disease conditions associated with asthma, e.g., airway hyperactivity, bronchial smooth muscle contraction, and extravasation of fluid from the vascular into the interstitial space of the lung. Inflammatory responses that accompany the asthmatic attack activate PKC in bronchial smooth muscle cells. Activation of PKC stimulates smooth muscle contraction including the smooth muscles of the respiratory tract (Itoh et al., 1993, *J. Physiol.* 397: 401; Peiper et al., 1996, *Pflugers Arch. Eur. J. Physiol.* 432: R47).

Mediators of inflammatory responses are thought to activate PKC by binding to their cognate receptors and activating a variety of signaling pathways which leads to productions of intracellular activators of PKC, e.g., diacylglycerol ( Blobe et al., 1996, *Cancer Surveys* 27: 213). PKC dependent contraction might be mediated by enhancing the phosphorylation of myosin light chain kinase either due to a direct phosphorylation process (Itoh et al., 1993, *J Physiol.* 397: 401) or to a decrease in the activity of myosin light chain kinase phosphatases (Cohen, 1989, *Proc. R. Soc. Lond. Biol.* 234: 115).

Extravasation of fluid may be mediated directly via PKC activation either by enhanced transcytosis, retraction of endothelial cells, or passage through the intercellular junctions (Lum et al., 1996, *Can. J Physiol. Pharmaco.l* 74: 787). PKC-β has been implicated as the PKC isoform responsible for increasing endothelial cell permeability (Nagpala et al., 1995, *J. Cell. Physiol.* 166: 249).

PKC inhibitors have been demonstrated to reduce smooth muscle contraction in diabetic rodents. In diabetes, PKC is chronically activated by the intracellular accumulation of diacylglycerol (Craven et al., 1989, *J. Clin. Invest.* 83:1667 and Craven, 1990, *Diabetes* 39: 667). A prolongation of the mean retinal circulation time is associated with the PKC activation and is thought to be due to enhanced smooth muscle contractile state which leads to an increase in vascular resistance (Ishii et al., 1996, *Science* 272: 728). Treatment of diabetic rodents with a PKC-β selective inhibitor normalized the prolonged retinal circulation time (Ishii et al., 1996).

Presently, no effective therapy is available for asthma. Elimination of the causative agent(s) from the environment of an allergic asthmatic is the most successful means available of treating this condition. Desensitization or immunotherapy with extracts of the suspected allergens also has enjoyed widespread favor, but controlled studies are limited and have not proved it to be highly effective.

The drugs thus far used in the treatment of asthma may be broken down into five major categories: methylxanthines, beta-adrenergic agonists, glucocorticoids, chromones, and anticholinergics. Because there are few controlled trials that have conclusively demonstrated the superiority of one regimen over the other, specific recommendations for therapy are difficult to make.

As one can appreciate, the presently available treatments for asthma are not completely effective. There remains a need in the art to develop additional therapies for asthma and the syndromes associated therewith.

SUMMARY OF INVENTION

It is an object of the invention to provide a method for treating asthma.

It is another object of the invention to provide a method for treating one or more syndromes associated with asthma.

It is yet another object of the invention to provide a method for inhibiting pulmonary vascular permeability.

It is still another object of the invention to provide a method for inhibiting airway hyperactivity.

It is still yet another object of the invention to provide a method for inhibiting bronchial smooth muscle contractility.

These and other objects of the invention are provided by one or more of the embodiments provided below.

In one embodiment of the invention there is provided a method for treating asthma which comprises administering to a mammal in need of such treatment a therapeutically effective amount of at least one member of a particular class of protein kinase C inhibitors.

In another embodiment of the invention there is provided a method for treating one or more syndromes associated with asthma which comprises administering to a mammal in need of such treatment a therapeutically effective amount of the protein kinase C inhibitor.

In yet another embodiment of the invention there is provided a method for inhibiting pulmonary vascular permeability which comprises administering to a mammal in need of such treatment a therapeutically effective amount of the protein kinase C inhibitor.

In still another embodiment of the invention there is provided a method for inhibiting airway hyperactivity which comprises administering to a mammal in need of such treatment a therapeutically effective amount of the protein kinase C inhibitor.

In still yet another embodiment of the invention there is provided a method for inhibiting bronchial smooth muscle contractility which comprises administering to a mammal in need of such treatment a therapeutically effective amount of the protein kinase C inhibitor.

The present invention identifies protein kinase C inhibitor compounds which are effective in treating asthma and syndromes associated therewith.

DETAILED DESCRIPTION OF THE INVENTION

It is a discovery of the present invention that the therapeutic use of a particular class of protein kinase C inhibitors, i.e., inhibitors of the β isozyme of protein kinase C, and especially β isozyme selective inhibitors of PKC, inhibits pulmonary vascular permeability, bronchial smooth muscle contractility, and airway hyperactivity. Consequently, such compounds can be used therapeutically to treat asthma and syndromes associated therewith.

The method of this invention preferably utilizes those protein kinase C inhibitors that effectively inhibit the β isozyme. One suitable group of compounds are generally described in the prior art as bis-indolylmaleimides or macrocyclic bis-indolylmaleimides. Bis-indolylmaleimides well recognized in the prior art include those compounds described in U.S. Pat. Nos. 5,621,098, 5,552,396, 5,545,636, 5,481,003, 5,491,242, and 5,057,614, all incorporated by reference herein. Macrocyclic bis-indolylmaleimides are particularly represented by the compounds of formula I. These compounds, and methods for their preparation have been disclosed in U.S. Pat. No. 5,552,396, which is incorporated herein by reference. These compounds are administered in a therapeutically effective amount to a mammal, e.g., a human, to inhibit pulmonary vascular permeability, bronchial smooth muscle contractility, and/or airway hyperactivity, and thus to treat asthma and the syndromes associated therewith These compounds can also be administered to patients at risk of the disease conditions mentioned above as prophylactics.

One preferred class of compounds for use in the method of the invention has the formula (I):

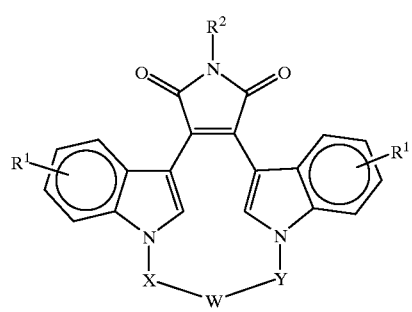

(I)

wherein:

W is —O—, —S—, —SO—, —SO$_2$—, —CO—, C$_2$–C$_6$ alkylene, substituted alkylene, C$_2$–C$_6$ alkenylene, -aryl-, -aryl(CH$_2$)$_m$O—, -heterocycle-, -heterocycle-(CH$_2$)$_m$O—, -fused bicyclic-, -fused bicyclic-(CH$_2$)$_m$O—, —NR$^3$—, —NOR$^3$—, —CONH—, or —NHCO—;

X and Y are independently C$_1$–C$_4$ alkylene, substituted alkylene, or together X, Y, and W combine to form -(CH$_2$)$_n$—AA—;

R$^1$s are hydrogen or up to four optional substituents independently selected from halo, C$_1$–C$_4$ alkyl, hydroxy, C$_1$–C$_4$ alkoxy, haloalkyl, nitro, —NR$^4$R$^5$, or —NHCO(C$_1$–C$_4$ alkyl);

R$^2$ is hydrogen, CH$_3$CO—, —NH$_2$, or hydroxy;

R$^3$ is hydrogen, —(CH$_2$)$_m$aryl, —C$_1$–C$_4$ alkyl, —COO (C$_1$–C$_4$ alkyl), —CONR$^4$R$^5$, —(C=NH)NH$_2$, —SO (C$_1$–C$_4$ alkyl), —SO$_2$ (NR$^4$R$^5$), or —SO$_2$ (C$_1$–C$_4$ alkyl);

R$^4$ and R$^5$ are independently hydrogen, C$_1$–C$_4$ alkyl, phenyl, benzyl, or combine with the nitrogen to which they are bonded to form a saturated or unsaturated 5 or 6 member ring;

AA is an amino acid residue;

m is independently 0, 1, 2, or 3; and n is independently 2, 3, 4, or 5, or a pharmaceutically acceptable salt, prodrug or ester thereof.

A more preferred class of compounds for use in this invention is represented by formula I wherein the moieties —X—W—Y—contain 4 to 8 atoms, which may be substituted or unsubstituted. Most preferably, the moieties —X—W—Y—contain 6 atoms.

Other preferred compounds for use in the method of this invention are those compounds of formula I wherein R$^1$ and R$^2$ are hydrogen; and W is a substituted alkylene, —O—, S—, —CONH—, —NHCO—or —NR$^3$—. Particularly preferred compounds for use in the invention are compounds of the formula Ia:

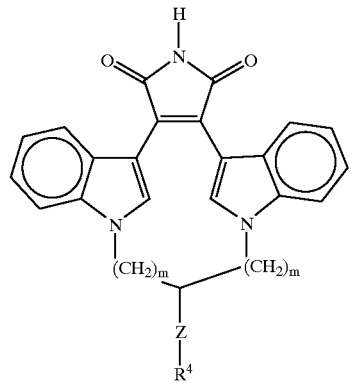

(Ia)

wherein Z is —(CH$_2$)$_p$— or —(CH$_2$)$_p$—O—(CH$_2$)$_p$—; R$^4$ is hydroxy, —SH, C$_1$–C$_4$ alkyl, (CH$_2$)$_m$aryl, —NH(aryl), —N(CH$_3$)(CF$_3$), —NH(CF$_3$), or —NR$^5$R$^6$; R$^5$ is hydrogen or C$_1$–C$_4$ alkyl; R$^6$ is hydrogen, C$_1$–C$_4$ alkyl or benzyl; p is 0, 1, or 2; and m is independently 2 or 3, or a pharmaceutically acceptable salt, prodrug or ester thereof. Most preferred compounds of the formula Ia are those wherein Z is CH$_2$; and R$^4$ is —NH$_2$, —NH(CF$_3$), or —N(CH$_3$)$_2$, or a pharmaceutically acceptable salt, prodrug or ester thereof.

Other preferred compounds for use in the method of the present invention are compounds wherein W in formula I is —O—, Y is a substituted alkylene, and X is an alkylene. These preferred compounds are represented by formula Ib:

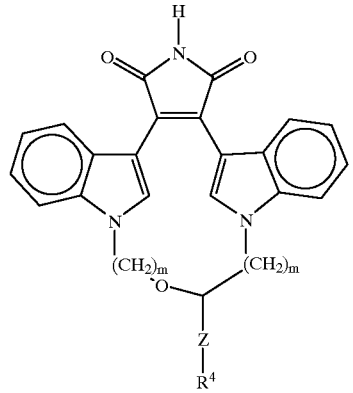

(Ib)

wherein Z is —(CH$_2$)$_p$—; R$^4$ is —NR$^5$R$^6$, —NH(CF$_3$), or —N(CH$_3$) (CF$_3$); R$^5$ and R$^6$ are independently H or C$_1$–C$_4$ alkyl; p is 0, 1, or 2; and m is independently 2 or 3, or a pharmaceutically acceptable salt, prodrug or ester thereof. Most preferred compounds of formula Ib are those wherein p is 1; and $R^5$ and $R^6$ are methyl.

Because they contain a basic moiety, the compounds of formulae I, Ia, and Ib can also exist as pharmaceutically acceptable acid addition salts. Acids commonly employed to form such salts include inorganic acids such as hydrochloric, hydrobromic, hydroiodic, sulfuric and phosphoric acid, as well as organic acids such as para-toluenesulfonic, methanesulfonic, oxalic, para-bromophenylsulfonic, carbonic, succinic, citric, benzoic, acetic acid, and related inorganic and organic acids. Such pharmaceutically acceptable salts thus include sulfate, pyrosulfate, bisulfate, sulfite, bisulfite, phosphate, mono-hydrogenphosphate, dihydrogenphosphate, metaphosphate, pyrophosphate, chloride, bromide, iodide, acetate, propionate, decanoate, caprylate, acrylate, formate, isobutyrate, heptanoate, propiolate, oxalate, malonate, succinate, suberate, sebacate, fumarate, maleate, 2-butyne-1,4-dioate, 3-hexyne-2, 5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, β-hydroxybutyrate, glycolate, maleate, tartrate, methanesulfonate, propanesulfonate, naphthalene-1-sulfonate, naphthalene-2-sulfonate, mandelate and the like. Particularly the hydrochloric and mesylate salts are used.

In addition to pharmaceutically-acceptable salts, other salts also can exist. They may serve as intermediates in the purification of the compounds, in the preparation of other salts, or in the identification and characterization of the compounds or intermediates.

The pharmaceutically acceptable salts of compounds of formulae I, Ia, and Ib can also exist as various solvates, such as with water, methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent.

It is recognized that various stereoisomeric forms of the compounds of formulae I, Ia, and Ib may exist; for example, W may contain a chiral carbon atom in the substituted alkylene moiety. The compounds are normally prepared as racemates and can conveniently be used as such. Alternatively, both individual enantiomers can be isolated or synthesized by conventional techniques if so desired. Such racemates and individual enantiomers and mixtures thereof form part of the compounds used in the methods of the present invention.

The compounds utilized in this invention also encompass the pharmaceutically acceptable prodrugs of the compounds of formulae I, Ia, and Ib. A prodrug is a drug which has been chemically modified and may be biologically inactive at its site of action, but which may be degraded or modified by one or more enzymatic or other in vivo processes to the parent bioactive form. This prodrug likely may have a different pharmacokinetic profile than the parent, enabling easier absorption across the mucosal epithelium, better salt formation or solubility, and/or improved systemic stability (an increase in plasma half-life, for example). Typically, such chemical modifications include the following:

1) ester or amide derivatives which may be cleaved by esterases or lipases;
2) peptides which may be recognized by specific or nonspecific proteases; or
3) derivatives that accumulate at a site of action through membrane selection of a prodrug form or a modified prodrug form; or any combination of 1 to 3, supra. Conventional procedures for the selection and preparation of suitable prodrug derivatives are described, for example, in H. Bundgaard, Design of Prodrugs, (1985).

The synthesis of various bis-indole-N-maleimide derivatives is described in Davis et al. U.S. Pat. No. 5,057,614 and the synthesis of the preferred compounds suitable for use in this invention are described in the previously identified U.S. Pat. No. 5,552,396 and in Faul et al. EP publication 0 657 411 A1, all of which are incorporated herein by reference.

One particularly preferred protein kinase -β inhibitor for use in the method of this invention is the compound described in Example 5 g ((S)-3,4-[N,N'-1,1'-((2"-ethoxy)-3'''(O)-4'''-(N,N-dimethylamino)-butane)-bis-(3,3'-indolyl)]-1(H)-pyrrole-2,5-dione Hydrochloride Salt) of the aforementioned U.S. Pat. No. 5,552,396. This compound is a potent protein kinase C inhibitor. It is selective to protein kinase C over other kinases and is highly isozyme-selective, i.e., it is selective for the beta-1 and beta -2 isozymes. Other salts of this compound also would be favored, especially the mesylate salts, as described in U.S. Pat. No. 5,710,145 (incorporated herein by reference).

A preferred mesylate salt can be prepared by reacting a compound of the formula II:

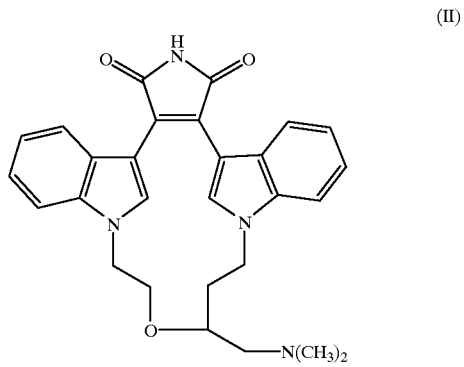

(II)

with methanesulfonic acid in a non-reactive organic solvent, preferably an organic/water mixture, and most preferably water-acetone. Other solvents such as methanol, acetone, ethylacetate and mixtures thereof are operable. The ratio of solvent to water is not critical and generally determined by the solubility of the reagents. Preferred solvent to water ratios are generally from 0.1:1 to 100:1 solvent to water by volume. Preferably, the ratio is 1:1 to 20:1 and most preferably 5:1 to 10:1. The optimal ratio is dependent on the solvent selected and is preferably acetone at a 9:1 solvent to water ratio.

The reaction usually involves approximately equimolar amounts of the two reagents, although other ratios, especially those wherein the methanesulfonic acid is in excess, are operative. The rate of addition of methanesulfonic acid is not critical to the reaction and may be added rapidly (<5 minutes) or slowly over 6 or more hours. The reaction is carried out at temperatures ranging from 0° C. to reflux. The reaction mixture is stirred until formation of the salt is complete, as determined by X-ray powder diffraction and can take from 5 minutes to 12 hours.

The salts of the present invention are preferably and readily prepared as a crystalline form. The trihydrate form of the salt may be readily converted to the monohydrate upon drying or exposure to 20–60% relative humidity. The salt is substantially crystalline demonstrating a defined melting point, birefringence, and an x-ray diffraction pattern.

Generally, the crystals have less than 10% amorphous solid and preferably less than 5% and most preferably less than 1% amorphous solid.

The mesylate salt is isolated by filtration or other separation techniques appreciated in the art, directly from the reaction mixture in yields ranging from 50% to 100%. Recrystallization and other purification techniques known in the art may be used to purify the salt further if desired.

The inhibitors of the β isozyme of PKC described in the present invention can be used to inhibit pulmonary vascular permeability, bronchial smooth muscle contractility, and airway hyperactivity, and generally to treat asthma.

Asthma is a respiratory tract condition characterized by enhanced pulmonary vascular permeability and bronchial smooth muscle contractility. Increases in bronchial smooth muscle contractility leads to airway hyperactivity. Enhanced pulmonary vascular permeability causes extravasation of fluid into the extravascular space which acts as a barrier for the diffusion of oxygen from the airway into the blood.

Asthma is manifested physiologically by a widespread narrowing of the air passages which may be relieved spontaneously or as a result of therapy. Asthma is manifested clinically by paroxysms of dyspnea, cough, wheezing, shortness of breath, hypoxemia, and in severe cases, status asthmaticus, resulting in death. It is an episodic disease, acute exacerbations being interspersed with symptom-free periods. Typically, most attacks are short-lived, lasting minutes to hours, however, there can be a phase in which the patient experiences some degree of airway obstruction daily.

Asthma can be broadly divided into two groups: allergic and idiosyncratic. Allergic asthma is dependent upon an IgE response controlled by T and B lymphocytes and activated by the interaction of antigen with mast cell-bound IgE molecules. Allergic asthma is often associated with a personal and/or family history of allergic diseases such as rhinitis, urticaria, and eczema; positive wheal-and-flare skin reactions to intradermal injection of extracts of airborne antigens; increased levels of IgE in the serum; and/or positive response to provocation tests involving the inhalation of specific antigen.

A significant segment of the asthmatic population will present with negative family or personal histories of allergy, negative skin tests, and normal serum levels of IgE, and therefore cannot be classified on the basis of defined immunologic mechanisms. These are termed idiosyncratic asthma. Many of these will develop a typical symptom complex upon contracting an upper respiratory illness.

Although asthma is primarily a disease of airways, virtually all aspects of pulmonary function are compromised during an acute attack. The pathophysiologic hallmark of asthma is a reduction in airway diameter brought about by contraction of smooth muscle, edema of the bronchial wall, and thick tenacious secretions. The syndromes or disease conditions associated with asthma include an increase in airway resistance, decreased forced expiratory volumes and flow rates, hyperinflation of the lungs and thorax, increased work of breathing, changes in elastic recoil of the lung tissue, abnormal distribution of both ventilation and pulmonary blood flow, mismatched ratios, and altered arterial blood gases. In addition, in very symptomatic patients there frequently is electrocardiographic evidence of right ventricular hypertrophy.

One skilled in the art will recognize that a therapeutically effective amount of the protein kinase C inhibitor of the present invention is the amount sufficient to inhibit pulmonary vascular permeability, bronchial smooth muscle contractility, and airway hyperactivity. Such amount varies inter alia, depending upon the concentration of the compound in the therapeutic formulation, the body weight of the patient, the condition of the patient and the method of application.

Generally, an amount of protein kinase C inhibitor to be administered as a therapeutic agent will be determined on a case by case basis by the attending physician. As a guideline, the causative agent(s) of an asthma attack, the degree of syndromes derived from an asthma attack, the duration of an asthma attack, the association of an asthma attack with other diseases, the body weight, and the age of a patient, the mode of administration, and the like will be considered when setting an appropriate dose. Some other factors to be considered as reference are the patients hypertension, smoking habit, and overall vascular condition.

Generally, a suitable dose is one that results in a concentration of the protein kinase C inhibitor at the treatment site in the range of 0.5 nM to 200 μM, and more usually between about 0.5 nM to 200 nM. It is expected that serum concentrations of 0.5 nM to 20 nM should be sufficient in many circumstances.

To obtain these treatment concentrations, a patient in need of treatment likely will be administered between about 0.001 mg per day per kg of body weight and 50.0 mg per day per kg. Usually, not more than about 10.0 mg per day per kg of body weight of protein kinase C inhibitor should be needed in many cases. As noted above, the above amounts may vary on a case-by-case basis.

The therapeutic effects provided by the present invention can be evaluated by examining the effects of the PKC isozyme selective inhibitors in several test models or systems. Specifically, the effects of the compounds of formula I and the preferred compounds of formula Ia and Ib on vascular permeability and formation of diacylglycerol, e.g., histamine or thrombin. For example, an inhibition or blockage of VEGF/VPF induced increases in vascular permeability in an in vivo system is predictive of a positive response in preventing or inhibiting asthma attack. An inhibition of diacylglycerol formation in cultured microvascular endothelial cells treated with PKC activators is predictive of a positive response in preventing or inhibiting asthma attack in vivo.

The effects of the compounds on asthma and the syndromes associated therewith can also be evaluated in animal models. An animal may be challenged with an allergen via the cutaneous route to which it has been previously sensitized. The animals then may be treated with a placebo or with the PKC-β selective inhibitor after the initial sensitization. Subsequently, the animals may be rechallenged with the antigen against which they had been previously immunized. The inflammatory response and fluid extravasation can be measured by the size of the cutaneous reaction. The challenge site can also be directly assessed for increases in vascular permeability. The ability of a PKC-β selective inhibitor to reduce the cutaneous reaction or vascular permeability upon rechallenge with the antigen would demonstrate the utility of the inhibitors in treating asthma.

To assess the efficacy of a PKC-β selective inhibitor on antagonizing or inhibiting vascular permeability, the cutaneous permeability stimulated by bronchial lavage fluid produced by asthmatic animals could be examined. Bronchial lavage fluid from acutely asthmatic animals can be cutaneously injected into non allergic animals treated with a placebo or with a PKC-β selective inhibitor. The ability of a PKC-β selective inhibitor to reduce vascular permeability induced by the bronchial lavage fluid of a asthmatic animal is predictive of a positive response of inhibiting the permeability stimulated by the inflammatory factors released during the asthmatic state.

The effectiveness of a PKC-β selective inhibitor in treating asthma can also be assessed by examining the bronchial reactivity of animals challenged with an allergen. Animals sensitized to an allergen can be treated with a placebo or with a PKC-β selective inhibitor. Subsequently, these animals can be challenged with the allergen and monitored for their pulmonary functions. The ability of a PKC-β selective inhibitor to reduce bronchial reactivity would be predictive of the effectiveness of the PKC inhibitor in treating asthma.

The compounds of formula I, and the preferred compounds of formula Ia and Ib are preferably formulated prior to administration. Suitable pharmaceutical formulations are prepared by known procedures using well known and readily available ingredients. In making the compositions suitable for use in the method of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders for either oral or topical application.

Some examples of suitable carriers, excipient, and diluents include lactose, dextrose, sucrose sorbitol, mannitol, starches, gum acacia, calcium phosphates, alginate, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient. The compositions are preferably formulated in a unit dosage form, each dosage containing from about 0.05 mg to about 3 g, more usually about 5–15 mg of the active ingredient. However, it will be understood that the therapeutic dosage administered will be determined by the physician in the light of the relevant circumstances including the severity of the condition to be treated, the choice of compound to be administered and the chosen route of administration. Therefore, the above dosage ranges are not intended to limit the scope of the invention in any way. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

In addition to the above formulations, most of which may be administered orally, the compounds used in the method of the present invention also may be administered topically. Topical formulations include ointments, creams and gels. In a preferred embodiment, intracavernosal injection of the compound directly to the smooth muscle is used.

Ointments generally are prepared using either (1) an oleaginous base, i.e., one consisting of fixed oils or hydrocarbons, such as white petrolatum or mineral oil, or (2) an absorbent base, i.e., one consisting of an anhydrous substance or substances which can absorb water, for example anhydrous lanolin. Customarily, following formation of the base, whether oleaginous or absorbent, the active ingredient (compound) is added to an amount affording the desired concentration.

Creams are oil/water emulsions. They consist of an oil phase (internal phase), comprising typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate; hydrophilic colloids, such as acacia colloidal clays, veegum, and the like. Upon formation of the emulsion, the active ingredient (compound) customarily is added in an amount to achieve the desired concentration.

Gels comprise a base selected from an oleaginous base, water, or an emulsion-suspension base. To the base is added a gelling agent which forms a matrix in the base, increasing its viscosity. Examples of gelling agents are hydroxypropyl cellulose, acrylic acid polymers, and the like. Customarily, the active ingredient (compounds) is added to the formulation at the desired concentration at a point preceding addition of the gelling agent.

The amount of compound incorporated into a topical formulation is not critical; the concentration should be within a range sufficient to permit ready application of the formulation to the affected tissue area in an amount which will deliver the desired amount of compound to the desired treatment site.

The customary amount of a topical formulation to be applied to an affected tissue will depend upon concentration of compound in the formulation. Generally, the formulation will be applied to the effected tissue in an amount affording from about 1 to about 500 µg compound per $cm^2$ of an affected tissue. Preferably, the applied amount of compound will range from about 30 to about 300 µg/$cm^2$, more preferably, from about 50 to about 200 µg/$cm^2$, and, most preferably, from about 60 to about 100 µg/$cm^2$.

The following formulation examples are illustrative only and are not intended to limit the scope of the invention in any way.

Formulation 1

Hard gelatin capsules are prepared using the following ingredients:

|  | Quantity (mg/capsule) |
|---|---|
| Active agent | 5 |
| starch, dried | 200 |
| magnesium stearate | 10 |
| Total | 215 mg |

The above ingredients are mixed and filled into hard gelatin capsules in 460 mg quantities.

Formulation 2

A tablet is prepared using the ingredients below:

|   | Quantity (mg/capsule) |
|---|---|
| Active agent | 15 |
| cellulose, microcrystalline | 10 |
| silicon dioxide, fumed | 10 |
| stearic acid | 5 |
| Total | 40 mg |

The components are blended and compressed to form tablets each weighing 665 mg.

Formulation 3

Tablets each containing 60 mg of active ingredient are made as follows:

|   | Quantity (mg/tablet) |
|---|---|
| Active agent | 60 mg |
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

What is claimed is:

1. A method for treating asthma which comprises administering to a mammal in need of such treatment, a therapeutically effective amount of an inhibitor of the β isozyme of protein kinase C.

2. The method of claim 1 wherein the inhibitor of the β isozyme of protein kinase C is a bis-indolylmaleimide or a macrocyclic bis-indolylmaleimide.

3. The method of claim 1 wherein the inhibitor is β-isozyme selective and where the isozyme selectivity is selected from the group consisting of beta-1 and beta-2 isozymes.

4. The method of claim 3 wherein the protein kinase C inhibitor has the following formula:

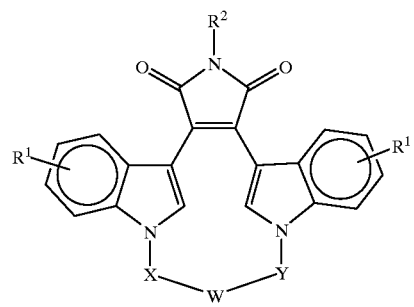

(I)

wherein:

W is —O—, —S—, —SO—, —SO$_2$—, —CO—, $C_2$-$C_6$ alkylene, substituted alkylene, $C_2$-$C_6$ alkenylene, -aryl-, -aryl(CH$_2$)$_m$O—, -heterocycle-, -heterocycle-(CH$_2$)$_m$O—, -fused bicyclic-, -fused bicyclic-(CH$_2$)$_m$O—, —NR$^3$—, —NOR$^3$—, —CONH—, or —NHCO—;

X and Y are independently $C_1$-$C_4$ alkylene, substituted alkylene, or together X, Y, and W combine to form —(CH$_2$)$_n$—AA—;

R$^1$s are hydrogen or up to four optional substituents independently selected from halo, $C_1$-$C_4$ alkyl, hydroxy, $C_1$-$C_4$ alkoxy, haloalkyl, nitro, NR$^4$R$^5$, or —NHCO($C_1$-$C_4$ alkyl);

R$^2$ is hydrogen, CH$_3$CO—, NH$_2$, or hydroxy;

R$^3$ is hydrogen, —(CH$_2$)$_m$aryl, —$C_1$-$C_4$ alkyl, —COO ($C_1$-$C_4$ alkyl), —CONR$^4$R$^5$, —(C=NH)NH$_2$, —SO ($C_1$-$C_4$ alkyl), —SO2 (NR$^4$R$^5$), or —SO$_2$ ($C_1$-$C_4$ alkyl);

R$^4$ and R$^5$ are independently hydrogen, $C_1$-$C_4$ alkyl, phenyl, benzyl, or combine to the nitrogen to which they are bonded to form a saturated or unsaturated 5 or 6 member ring;

AA is an amino acid residue;

m is independently 0, 1, 2, or 3; and n is independently 2, 3, 4, or 5 or a pharmaceutically acceptable salt, prodrug or ester thereof.

5. The method of claim 4 wherein the protein kinase C inhibitor has the following formula:

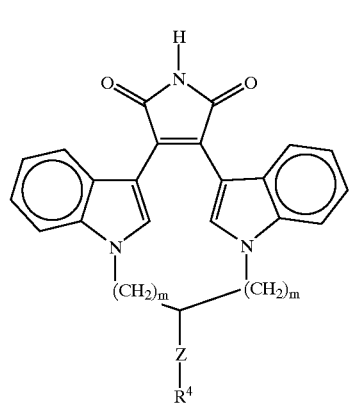

(Ia)

wherein Z is —(CH$_2$)$_p$—or —(CH$_2$)$_p$—O—(CH$_2$)$_p$—; R$^4$ is hydroxy, —SH, $C_1$-$C_4$ alkyl, (CH$_2$)$_m$aryl, —NH(aryl), —N(CH₃)(CF₃), —NH(CF₃), or —NR⁵R⁶; R⁵ is hydrogen or C₁–C₄ alkyl; R⁶ is hydrogen, C₁–C₄ alkyl or benzyl; p is 0, 1, or 2; and m is independently 2 or 3, or a pharmaceutically acceptable salt, prodrug or ester thereof.

6. The method of claim 4 wherein the protein kinase C inhibitor has the following formula:

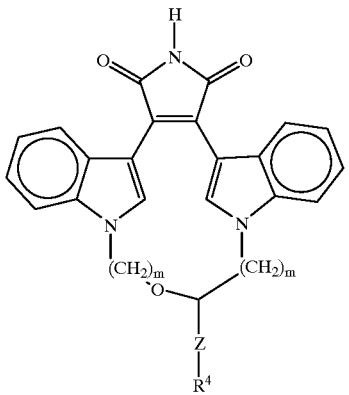

(Ib)

wherein Z is —(CH₂)$_p$—; R⁴ is —NR⁵R⁶, —NH(CF₃), or —N(CH₃)(CF₃); R⁵ and R⁶ are independently H or C₁–C₄ alkyl; p is 0, 1, or 2; and m is independently 2 or 3, or a pharmaceutically acceptable salt, prodrug or ester thereof.

7. The method of claim 4, wherein the protein kinase C inhibitor comprises (S)-3,4-[N,N'-1,1'-((2"-ethoxy)-3'''(O)-4'''-(N,N-dimethylamino)-butane) -bis-(3,3'-indoly1)]-1(H)-pyrrole-2,5-dione or a pharmaceutically acceptable acid salt thereof.

8. A method for treating a syndrome associated with asthma which comprises administering to a mammal in need of such treatment, a therapeutically effective amount of an inhibitor of the β isozyme of protein kinase C.

9. The method of claim 8 wherein the syndrome is selected from the group consisting of paroxysms of dyspnea, cough, wheezing, shortness of breath, hypoxemia, an increase in airway resistance, decreased forced expiratory volumes and flow rates, hyperinflation of the lungs and thorax, increased work of breathing, changes in elastic recoil, abnormal distribution of both ventilation and pulmonary blood flow, mismatched ratios, altered arterial blood gases, and right ventricular hypertrophy.

10. A method for inhibiting pulmonary vascular permeability which comprises administering to a mammal in need thereof a therapeutically effective amount of an inhibitor of the β isozyme of protein kinase C.

11. A method for inhibiting airway hyperactivity which comprises administering to a mammal in need thereof a therapeutically effective amount of an inhibitor of the β isozyme of protein kinase C.

12. A method for inhibiting bronchial smooth muscle contractility which comprises administering to a mammal in need thereof a therapeutically effective amount of an inhibitor of the β isozyme of protein kinase C.

* * * * *

UNITED STATES PATENT AND TRADEMARK OFFICE
CERTIFICATE OF CORRECTION

PATENT NO. : 6,103,712
DATED : August 15, 2000
INVENTOR(S) : Douglas Kirk WAYS

It is certified that error appears in the above-identified patent and that said Letters Patent is hereby corrected as shown below:

In Claim 4, Column 12, line 34:

"SO2" has been replaced with --$SO_2$--.

Signed and Sealed this

First Day of May, 2001

Attest:

NICHOLAS P. GODICI

*Attesting Officer*     *Acting Director of the United States Patent and Trademark Office*